United States Patent [19]

Kajfež et al.

[11] 4,226,766
[45] Oct. 7, 1980

[54] NOVEL METHOD FOR PREPARING N(1)-ALKYLATED-5-PHENYL-7-SUBSTITUTED-2-DEOXY-1,4-BENZODIAZEPINES

[75] Inventors: Franjo Kajfež; Vitomir Sunjic; Vesna Caplar, all of Zagreb, Yugoslavia

[73] Assignee: CRC Compagnia di Recerca Chimica S.A., Chiasso, Switzerland

[21] Appl. No.: 928,833

[22] Filed: Jul. 27, 1978

Related U.S. Application Data

[63] Continuation of Ser. No. 740,075, Nov. 8, 1976, abandoned, and a continuation-in-part of Ser. No. 684,450, May 7, 1976, abandoned.

[30] Foreign Application Priority Data

May 12, 1975 [CH] Switzerland ........................ 6068/75

[51] Int. Cl.³ ............................................ C07D 243/16
[52] U.S. Cl. ...................... 260/239 BD; 260/570 AB; 260/574; 260/577; 260/583 R; 544/178; 548/335
[58] Field of Search ................. 260/239 BD, 247, 309, 260/570 AB, 577, 578, 283 R, 283 SY, 583 R

[56] References Cited

FOREIGN PATENT DOCUMENTS 1295209 11/1972 United Kingdom ............. 260/239 BD

OTHER PUBLICATIONS

Kanaoka et al., Tetrahedron, vol. 25, pp. 2757–2766 (1969).

*Primary Examiner*—Alton D. Rollins
*Attorney, Agent, or Firm*—Haseltine, Lake & Waters

[57] ABSTRACT

A method for preparing N(1)-alkylated-5-phenyl-7-substituted deoxy-1,4-benzodiazepines utilizing a polyphosphoric acid alkyl ester of the formula:

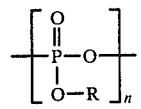

wherein $R_3$ is an alkyl radical with up to 4 carbon atoms as the alkylating agent, is described.

2 Claims, No Drawings

NOVEL METHOD FOR PREPARING N(1)-ALKYLATED-5-PHENYL-7-SUBSTITUTED-2-DEOXY-1,4-BENZODIAZEPINES

This is a continuation of U.S. patent application Ser. No. 740,075, filed Nov. 8, 1976, now abandoned, which, in turn, is a continuation-in-part of U.S. patent application Ser. No. 684,450, filed May 7, 1976 now abandoned.

The present invention relates to a a method for the preparation of compounds of the formula:

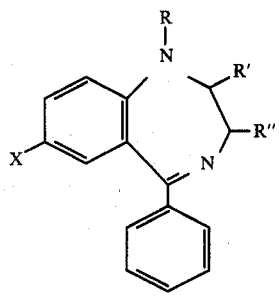

wherein R is an alkyl radical of not more than 4 carbon atoms, R' and R" are each a hydrogen atom or an alkyl group of up to 2 carbon atoms with the proviso that R', R" and the carbon atoms to which they are attached total no more than 4 carbon atoms, and X is a chloro group.

The method is characterized by performing an alkylative cyclization on a compound of the formula

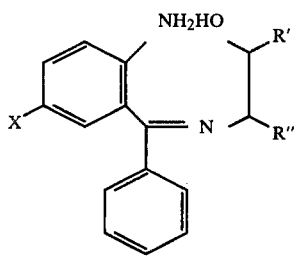

wherein R', R", and X are as defined above, with a polyphosphoric acid alkyl ester having the general formula:

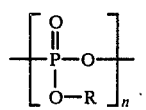

wherein R is an alkyl radical with not more than 4 carbon atoms, and by carrying out the alkylation at elevated temperatures, preferably between 120° and 160° C. and from 1.5 to 10 hours, depending on the alkylation medium. The reaction is conducted in the absence of a solvent or diluent.

The polyphosphoric acid esters of formula I may be prepared by known methods, for example according to Y. Kanaoka et al., Chem. Pharm. Bull., Japan 18, 397, 587 (1970), or P. Cava et al., J. Org. Chem., 34, 2665 (1969). Attention should be paid to the fact that these preparations require the use of anhydrous alcohols, and that it is advantageous if the work is carried out in a nitrogen atmosphere.

Esters so prepared from lower alcohols have a pronounced alkylating effect particularly at temperature above 120° to 140° C.

The compounds of formula II also include, in addition to a primary amino group, also an ω-hydroxyalkyl group of up to 4 carbon atoms, and the polyphosphoric acid esters of formula III may cause not only an intermolecular alkylation but also an additional intramolecular alkylation. The alkylation of a few 2-amino-benzophenon-β-hydroxyalkylamines, for example, resulted at 140° C. in cyclic N-(1)-alkyl-1,4-benzodiazepines (compounds a to f in the table). If the work is carried out at temperatures below 100° C., only a closure of the ring takes place but no intermolecular alkylation, a fact which is specified also in British Patent No. 1,295,209 (1972).

We have discovered, however, that at higher temperatures usually at 120°–160° C., these esters concomitantly raise the yield N(1) alkylation thus allowing isolation after one-pot preparation of various N(1)-alkylated-5-phenyl-7-substituted-2-deoxy-1,4-benzodiazepines, of the general formula I. This finding is surprising in view of the fact that in this particular temperature range, and carrying out reactions for the periods indicated in the examples, neither N(1) or N(4) quaternization nor acidic hydrolysis of the 4(N)-C(5) double bond occur. Moreover, the method according to the present invention is characterized by the fact that no racemization, or epimerization, takes place if optionally active starting compounds of the general formula II are used.

The method according to the present invention is characterized by the fact that no racemization takes place if optically active initial materials are used (see compounds e and f in the table).

This novel method permits a successful alkylation of all heterocyclic compounds containing at least one >NH-group such as, for example, various imidazole derivatives, 1,4-benzodiazepines, morpholino derivatives, etc. Moreover, it permits an alkylation of various aliphatic, aromatic, or combined aliphatic-aromatic amines such as, for example, diethyl amine, aniline, p-chloroaniline, ortho-(3-hydroxypropyl)-aniline, ortho-benzoyl-parachloro-aniline, etc. These examples show that the nature of the substituents in the aniline ring does not exert any determinable influence of the alkylating reaction.

The above statements indicate that polyphosphoric acid esters of formula III represent a group of extremely interesting alkylating agents which, among other things, have the following advantages: ready accessibility, good dissolving power for numerous organic substances, and formation of a poly-acid of medium strength during alkylation. By virtue of these properties no addition of organic solvents is required; however, the usual inert solvents may be advantageously added in certain cases, while it may be advantageous also if one adds bases, for example, organic tertiary amines, or inorganic hydroxides, as used up until now in some alkylating methods.

The following examples are intended to further explain the present invention.

The same alkylating method was employed in all the examples stated hereinafter, with the exception of the reaction temperature and duration which varied as stated in the table together with the initial compounds, alkylating agents and yields of resulting products. The method was carried out as follows:

N-alkylation with polyphosphoric acid esters

EXAMPLE 1 (Generalized Method)

The amino compound (0.10 to 0.15 mol) was added to the polyphosphoric acid ester (0.50 mol) in a nitrogen atmosphere. The reaction mixture was heated in such a way that an inner temperature of 120° C. was reached after approximately 1 to 1.5 hours. The reaction vessel was subjected to shaking from time to time so as to mix the viscous blend. Substantial foaming occurred during heating in some cases. After foaming had subsided heating was continued to a temperature increase of about 15° to 20° C. above the former. Excessively high temperatures must be avoided because this may cause a quaternization of the amino compounds, which development may be observed by means of thin-layer chromatography on the occurrence of a component that runs short in the reaction mixture. However, temperatures which are too low may strongly retard or even completely stop the alkylation.

The reaction durations at optimal temperatures employed in the examples are stated in the following table. The course or progress of the reaction may be observed by withdrawing a sample, mixing the same with ice water, pH-determination, extraction in organic solvents, and subsequent thin-layer control. After the reaction was completed the mixture was diluted with ice water and extracted with ether or acetic ester. The organic extract was dried, evaporated, and the residue purified. In cases in which no direct crystallization occurred it was found that a column chromatography on silica gel (Merck: 0.025 to 0.10 mm) is a highly effective purification method. The yields stated in the table relate to the isolated, thin-layer chromatographically pure products.

EXAMPLE 2

Compounds marked a, c, e, and f in the table are obtained from 0.5 mole of the methyl ester of polyphosphoric acid and 0.14 mole of the following compounds, respectively:

a = 2-amino-5-chloro(2'-hydroxyethylketimine)benzophenone
c = 2-amino-5-chloro-(2'-hydroxy-2'-methylethylketimine)-benzophenone
e = 2-amino-5-chloro-(1'-ethyl-2'-hydroxyethylketimine)-benzophenone
f = 2-amino-5-chloro-(1'-ethyl-2'-hydroxyethylketimine)-o'-fluoro-benzophenone.

The structure and characteristics of the resulting compounds are given in the table.

The table discloses the yield, temperature and the reaction time.

EXAMPLE 3

In accordance with the generalized example and starting with the ethyl ester of polyphosphoric acid, compounds j, b, d, and n are obtained (the characteristics being given in the table).

TABLE

| | Starting Compound | Alkyl Radical (R) | Product | Yield (%) | Reaction Conditions Temperature °C./Time hours | M.P. B.P. °C. |
|---|---|---|---|---|---|---|
| (a) | [structure: Cl-phenyl-NH2, =N-CH2-CH2-OH, with phenyl] | CH3 | [structure: Cl-phenyl-N(CH3)-CH2, =N, with phenyl] | 68 | 160/5 | 98–101 |
| (b) | [structure: Cl-phenyl-NH2, =N-CH2-CH2-OH, with phenyl] | CH2CH3 | [structure: Cl-phenyl-N(CH2CH3)-CH2, =N, with phenyl] | 69.5 | 160/5 | 215–218 |
| (c) | [structure: Cl-phenyl-NH2, =N-CH2-C(OH)(CH3), with phenyl] | CH3 | [structure: Cl-phenyl-N(CH3)-CH2-C(CH3), =N, with phenyl] (±) Racemate | 13.5 | 140/8 | 94–95.5 |
| (d) | [structure: Cl-phenyl-NH2, =N-CH2-C(OH)(CH3), with phenyl] | CH2CH3 | [structure: Cl-phenyl-N(CH2CH3)-CH2-C(CH3), =N, with phenyl] (±) (Racemate) | 46 | 140/8 | 205–210 |
| (e) | [structure: Cl-phenyl-NH2, =N-CH(CH2CH3)-CH2-OH, with phenyl] | CH3 | [structure: Cl-phenyl-N(CH3)-CH(CH2CH3)-CH2, =N, with phenyl] (35) | 55 | 140/8 | 114–115 |

TABLE-continued

| Starting Compound | Alkyl Radical (R) | Product | Yield (%) | Reaction Conditions Temperature and °C./Time hours | M.P. B.P. °C. |
|---|---|---|---|---|---|
| (f) 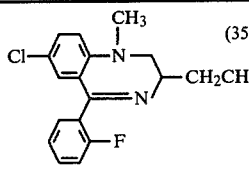 | CH$_3$ | (35) | 24.5 | 140/8 | 120–121 |

We claim:

1. A process for preparing compounds of the formulas:

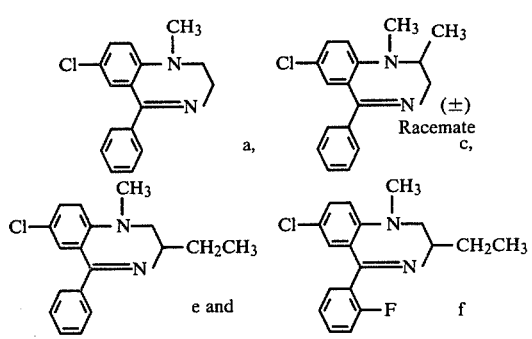

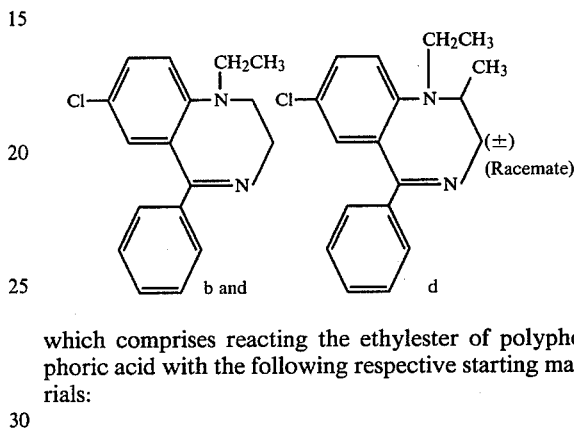

which comprises reacting 0.5 mole of the methyl ester of polyphosphoric acid with 0.14 mole of the appropriate respective starting materials, to wit:

a = 2-amino-5-chloro(2'-hydroxyethylketimine)-benzophenone for 5 hours at about 160° C.
c = 2-amino-5-chloro-(2'-hydroxy-2'-methylethylketimine)benzophenone for 8 hours at about 140° C.
e = 2-amino-5-chloro-(1'-ethyl-2'-hydroxyethylketimine)benzophenone for 8 hours at about 140° C.
f = 2-amino-5-chloro-(1'-ethyl-2'-hydroxyethylketimine)o-fluoro-benzophenone for 8 hours at about 140° C., respectively, and isolating the respective products.

2. A process for preparing the compounds of the formulas:

which comprises reacting the ethylester of polyphosphoric acid with the following respective starting materials:

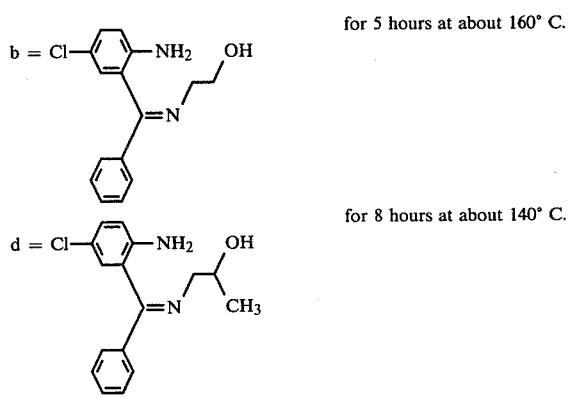

for 5 hours at about 160° C.

for 8 hours at about 140° C.

and isolating the respective products.

* * * * *